United States Patent [19]

Hikino et al.

[11] Patent Number: 4,801,582
[45] Date of Patent: * Jan. 31, 1989

[54] METHOD AND COMPOSITION FOR TREATING HYPOGLYCEMIA USING ALOE POLYSACCHARIDES

[75] Inventors: Hiroshi Hikino, Sendai; Teruaki Hayashi, Kawanishi, both of Japan

[73] Assignee: Toyo Yakushoku Kogyo Co., Ltd., Tokyo, Japan

[*] Notice: The portion of the term of this patent subsequent to Jul. 1, 2003 has been disclaimed.

[21] Appl. No.: 879,603

[22] Filed: Jun. 27, 1986

Related U.S. Application Data

[63] Continuation-in-part of Ser. No. 718,082, Apr. 1, 1985, Pat. No. 4,598,069.

[51] Int. Cl.⁴ ............................................. A61K 31/715
[52] U.S. Cl. ...................... 514/54; 514/866; 536/1.1; 536/123; 536/128
[58] Field of Search .................. 514/54, 866; 536/1.1, 536/123, 128

[56] References Cited

U.S. PATENT DOCUMENTS

| | | | |
|---|---|---|---|
| 3,360,511 | 12/1967 | Farkas | 514/54 |
| 3,470,109 | 9/1969 | Marsh, Jr. | 536/1.1 |
| 4,598,069 | 7/1986 | Hikino et al. | 514/54 |
| 4,735,935 | 4/1988 | McAnalley | 514/54 |

OTHER PUBLICATIONS

Rakhimov, D. et al.; Chemical Abstracts, vol. 94:136159g, (1981).
Rakhimov, D. et al.; Chemical Abstracts, vol. 86:86163r, (1977).
Yagi, A. et al.; Chemical Abstracts, vol. 100:117822u, (1984).
Hranisavljevic-Jakouljevic, M. et al.; Chemical Abstracts, vol. 96:31629y, (1982).
Mandal, G. et al.; Chemical Abstracts, vol. 100:99930w, (1984).

*Primary Examiner*—Ronald W. Griffin
*Assistant Examiner*—Nancy S. Carson
*Attorney, Agent, or Firm*—Bryan, Cave, McPheeters & McRoberts

[57] ABSTRACT

A hypoglycemic composition which contains as an effective component a polysaccharide named as Arboran A or B which has hypoglycemic activity and water solubility, and a method of treating diabetes comprising administering to a patient afflicted with diabetes a therapeutically effective amount of the above composition.

2 Claims, No Drawings

METHOD AND COMPOSITION FOR TREATING HYPOGLYCEMIA USING ALOE POLYSACCHARIDES

CROSS REFERENCE TO RELATED APPLICATION

This application is a continuation-in-part of application Ser. No. 718,082 filed Apr. 1, 1985, now U.S. Pat. No. 4,598,069.

BACKGROUND OF THE INVENTION

1. Field of the Invention

The present invention relates to a hypoglycemic composition comprising as its effective component a polysaccharide having hypoglycemic activity which lowers blood glucose value and being obtainable from aloes which are plants of the family Liliaceae.

2. Description of the Prior Art

It is well known that a crude drug prepared from aloes of the family Liliaceae is used as a laxative [Japanese Pharmacopeia, 9th edition (1976), D-55], whereas other medicinal efficacies thereof still remain to be clarified.

SUMMARY OF THE INVENTION

We have found that a crude drug from aloes has hypoglycemic activity and conducted further research. As a result, we obtained hypoglycemic polysaccharides from the water-soluble component of aloes of the family Liliaceae by dialyzing the soluble components to remove substances up to 24 angstroms in particle size.

Although the characteristics of the polysaccharides obtained differ slightly according to the kind of aloe used as the material, any of these polysaccharides has the following unique properties.

(i) Solubility in water.
(ii) Hypoglycemic activity.
(iii) Developing a pale yellowish red color when brought into contact with a mixture of 2% aqueous solution of phenol and concentrated sulfuric acid, and being positive when subjected to silver mirror reaction or exposed to Fehling's solution (testing for polysaccharides).
(iv) Being larger than 24 angstroms in particle size.

Further, from the inner liquid obtained from the above dialysis or the aqueous solution of the above polysaccharide, two polysaccharides designated Arboran A and Arboran B were isolated. Each of them has strong hypoglycemic activity and other characteristics which are detailedly described in the following Example 3.

Thus, the present invention provides a hypoglycemic composition comprising as its effective component a polysaccharide which has hypoglycemic activity and is a watersoluble component of aloes of the family Liliaceae, especially Arboran A or Arboran B, and a method of treating diabetes comprising administering to a patient afflicted with diabetes a therapeutically effective amount of the above composition.

DESCRIPTION OF THE PREFERRED EMBODIMENTS

Given below are aloes of the family Liliaceae which contain the polysaccharides of the present invention.

An arborescent aloe (*Aloe arboresens Mill* including *Aloe arborescence* var. natalensis), cape aloes (*Aloe ferox Mill.*, *Aloe vera L.* and *Aloe africana Mill.*), nathal aloes (*Aloe bainesii th. Dyer* and *Aloe soccotrina Lam.*), a zanzibar aloe (*Aloe perryi Baker*), a curacau aloe (*Aloe barbadensis Miller*), jaffarabad aloes (*Aloe vera L. chinensis Haw.* and *Aloe striatula Haw.*), etc. Of course, *Aloe arborescens Mill* is grown nowadays and is a material which is readily available.

As the material of the effective component of aloes to be used in this invention, all leaves or the whole of the plant may be used in a fresh state or as dried.

The effective component may be obtained in the following manner.

First, the material, as it is or as treated for de-fatting with a usual fat-dissolving solvent such as ethyl ether, is subjected to extraction with water or an aqueous organic solvent (in 1.5 to 4 times the amount of fresh material). While the extraction can be conducted with water satisfactorily, an aqueous organic solvent may be used to prevent the extract from decaying or to promote the extraction. Water and aqueous organic solvent may be used together. Useful organic solvents for preparing the aqueous organic solvent are lower alcohols such as methanol and ethanol. Depending on the kind of material, up to 50%, preferably up to 30%, of organic solvent is contained in the aqueous organic solvent. The extraction can be accelerated at an elevated temperature. Preferably the material is crushed or pulverized before use.

The extract obtained is dialyzed as it is or as concentrated at a reduced pressure. Alternatively, a solution is dialyzed, which is prepared by adding a lower alcohol to the extract or concentrate to precipitate the hypoglycemic component, filtering the precipitate off, washing the precipitate with ethanol and dissolving the product in water or an aqueous organic solvent. The dialysis is conducted by means of a seamless cellulose membrane tubing (36/32 type, Visking tube product of Union Carbide Corporation in U.S.A.) for removing substances up to 24 angstroms in particle size, using the extract, concentrate or solution as inner liquid and water as outer liquid (in 4 to 6 times the amount of the inner liquid). The dialysis is carried out for 2 to 3 days (while replacing the water continuously or at least once daily). Alternatively, a solution may be dialyzed which is prepared by evaporating the extract to dryness under a reduced pressure, dissolving the residue in water and removing the insolubles from the resulting solution.

Thus, the dialyzate is obtained as the inner liquid or the precipitate and if needed may be dried in vacuo to obtain a brown powder.

This dialyzate or a solution of the brown powder in water is further processed to obtain Arboran A and Arboran B.

That is, the above dialyzate or solution is subjected to gel filtration chromatography using, for example a Sepharose 6B column (Pharmacia Fine Chemicals), eluting with 0.1M NaCl solution to collect polysaccharide-rich fractions. The collected fractions are combined and concentrated, and further dialyzed.

The resulting dialyzate (inner liquid) is concentrated and then subjected to a chromatography using an anion exchange resin, for example a DEAE Toyopearl column (Toyo Soda Manufacturing Co., LTD.), first eluting with water to collect polysaccharide-rich fractions (G-1) and successively eluting gradiently with 0–0.5M NaCl aqueous solution to collect polysaccharide-rich fractions (G-2).

The collected fractions (G-1) are combined, concentrated and then subjected to gel filtration chromatography of, for example a Sephacryl S-200 column (Pharmacia Fine Chemicals), eluting with 0.1M Tris-HCl buffer (pH 7.0) containing 0.5M NaCl solution to collect polysaccharide-rich fractions. The collected fractions are combined and concentrated, and further dialyzed.

The resulting dialyzate (inner liquid) is evaporated to dryness in vacuo to obtain Arboran A as a white powder.

On the other hand, the collected fractions (G-2) are combined and concentrated, and further dialyzed. The resulting dialyzate (inner liquid) is concentrated and then subjected to gel filtration chromatography using, for example a Sephacryl S-200 column, eluting with 0.1M Tris-HCl buffer (pH 7.0) containing 0.5M NaCl to collect polysaccharide-rich fractions. The collected fractions are combined and concentrated, and further dialyzed.

The resulting dialyzate (inner liquid) is evaporated to dryness in vacuo to obtain Arboran B as a white powder.

We have found that the polysaccharide thus prepared has an outstanding hypoglycemic effect as will be described later but little or no side effect.

The dosage of the hypoglycemic composition of the present invention varies with the symptom. For oral administration to adults, the composition is given usually in an amount of 10 to 500 mg/day, preferably 30 to 300 mg/day, calculated as the active component, in two to three divided doses, whereby the contemplated effect can be obtained.

The hypoglycemic composition of the present invention comprises one or a mixture of polysaccharides and a solid or liquid excipient. The composition is given orally usually in the form of a powder, tablets including sublingual tablets, emulsion, encapsulated preparation, granules, pellets, liquid preparations (including fluid extract and syrup), etc. The composition may be given in the form of an injection solution. The solid or liquid excipient to be used is one already known in the art. Preferably, each unit of the preparation contains the abovementioned single dose of the present compound.

Examples of excipients useful for powder, granular, or other oral preparation are lactose, starch, dextrin, calcium phosphate, calcium carbonate, synthetic and natural aluminum silicates, magnesium oxide, dry aluminum hydroxide, magnesium stearate, sodium bicarbonate, dry yeasts, etc.

This invention further includes cutaneously absorbable preparations formulated with use of usual excipients.

The preparations as mentioned above may be formulated by the conventional methods.

The polysaccharides of the invention are usable as health food containing the compound in an amount useful for keeping health but not producing a therapeutic effect. The compound is then given in a suitable form such as a liquid, granules, tea, usual capsules, soft capsules or the like.

The present invention will be described with reference to the following examples and animal experiment.

EXAMPLE 1

A 2 kg quantity of fresh *Aloe vera L.* was slightly dried in air, crushed and then immersed overnight in a mixture of about 5 liters of water and ethanol (1:1) at room temperature for extraction. The material was extracted in this manner two times, and thereafter three times similarly with use of water only. The collected extracts were filtered, and the combined filtrate was concentrated to about 2 liters in a vacuum by evaporating the solvent off. (If the filtrate bubbles up, a small amount of n-butanol is added.) The concentrate obtained was filtered to remove the insolubles. The filtrate was placed into a cellulose dialyzing membrane, 36/32 type Visking tube, and dialyzed for 3 days using from 10 liters of water as the outer liquid. (The outer liquid was replaced at least once daily.) The resulting dialyzate (inner liquid) was distilled in a vacuum to remove the solvent and then dried overnight in a desiccator, giving a brown powder (4.9 g). The product is a polysaccharide having the following properties and also having the hypoglycemic activity to be stated later.

(i) Infrared absorption spectrum (KBr method): $\nu$max: 3370, 1730, 1600, 1235 and 1040 cm$^{-1}$.

| (ii) Ultraviolet absorption | | | |
| --- | --- | --- | --- |
| $\lambda^{H2O}_{max}$ | 275 nm | $E^{0.05\%}_{1\,cm}$: | 12 |
| $\lambda^{H2O}_{max}$ | 295 nm | $E^{0.05\%}_{1\,cm}$: | 12 |

(iii) NMR spectrum (90 MHz, D$_2$O): 5.12(s), 5.03–4.64(m), 4.59(s), 4.43(s), 4.13(s), 3.49(s), 2.05(s), 1.88(s), 1.49(s) and 1.27(d, j=7).

(iv) pH: Having a pH of 4.75 when 100 mg of the product is dissolved in 10 ml of distilled water.

(v) Decomposition temperature: 240° C.

(vi) Solubility: Being soluble in water and insoluble in benzene, ether, chlorofrom, alcohols and acetone.

(vii) Color reaction: Developing a pale yellowish red color on contact with a mixture of 2% aqueous solution of phenol and concentrated sulfuric acid, and being positive for silver mirror reaction and Fehling's solution.

EXAMPLE 2

A brown powder was prepared from *Aloe arborescens Mill.* in the same manner as above. The product is also a polysaccharide having the following properties and further having the hypoglycemic activity to be stated later.

(i) Infrared absorption spectrum (KBr method): $\nu$max: 3300, 1590, 1410, 1240, 1050 and 600(broad) cm$^{-1}$.

| (ii) Ultraviolet absorption | | | |
| --- | --- | --- | --- |
| $\lambda^{H2O}_{max}$ | 275 nm | $E^{0.01\%}_{1\,cm}$: | 50 |
| $\lambda^{H2O}_{max}$ | 305 nm | $E^{0.01\%}_{1\,cm}$: | 50 |

(iii) NMR spectrum (90 MHz, D$_2$O): 5.25(s), 5.21–4.35(m), 4.21(s), 3.92–3.45(m), 2.39(s), 2.07(s), 1.85(s), 1.50(s), 1.25(s).

(iv) pH: Having a pH of 4.95 when 100 mg of the product is dissolved in 10 ml of distilled water.

(v) Decomposition temperature: 240° C.

(vi) Solubility: Being soluble in water and insoluble in benzene, ether, chloroform, alcohols and acetone.

(vii) Color reaction: Developing a pale yellowish red color on contact with a mixture of 2% aqueous solution of phenol and concentrated sulfuric acid, and being positive for silver mirror reaction and Fehling's solution.

TEST FOR PHARMACOLOGICAL EFFECT

Normal mice (Std. ddY strain, weighing 25 to 30 g) were divided into groups each consisting of 5 mice. The blood of each mouse was collected from the vein of the fundus oculi by a hematocrit tube and immediately centrifuged at 12000 r.p.m. for 5 minutes to obtain plasma. With use of glucose analyzer (Iatron M-7000, product of Dia-Iatron Co., Ltd.), the amount of glucose in the plasma was measured as the blood glucose value before the administration of the test specimen (0 hr.). Immediately after the collection of blood at 0 hr., a solution of the test specimen dissolved in physiological saline was intraperitoneally given to the mouse.

Seven hrs. and 24 hrs. after the administration of the specimen, the blood was collected, the amount of glucose in the plasma was measured, and the blood glucose value was calculated relative to that of 0 hr. which was taken as 100. The results are shown in Table 1, in which each relative value is expressed in average±standard error. The significance difference was determined by one-way variance analysis.

TABLE 1

| Test specimen | Dose (mg/kg) | Relative blood glucose value | | |
|---|---|---|---|---|
| | | 0 hr. | 7 hrs. | 24 hrs. |
| Control | 0 | 100 | 115±6.8 | 110±7.3 |
| Polysaccharide of Aloe vera L. prepared above | 100 | 100 | 66±4.9*** | 87±8.5 |
| Polysaccharide of Aloe arborescens Mill prepared above | 100 | 100 | 54±2.8*** | 74±1.8** |

Note:
n = 5; P < 0.01, *P < 0.001; Blood glucose value at 0 hr: 140-170 mg/ml The polysaccharides were isolated from other Aloes by the same process as that in the above Examples and subjected to the same pharmacological test as mentioned above. The results are given in Table 2.

TABLE 2

| Test specimen | Dose (mg/kg) | Relative blood glucose value | | |
|---|---|---|---|---|
| | | 0 hr | 7 hrs | 24 hrs |
| control | — | 100 | 105 ± 3 | 104 ± 4 |
| Aloe africana (Japan) | 100 | 100 | 67 ± 3** | 78 ± 7 |
| Aloe barbadensis (Japan) | 100 | 100 | 48 ± 3** | 68 ± 3** |
| Aloe barbadensis (India) | 100 | 100 | 60 ± 3** | 82 ± 5 |
| Aloe ferox (Japan) | 100 | 100 | 64 ± 3** | 94 ± 3 |
| Aloe peryii (India) | 100 | 100 | 77 ± 1** | 80 ± 7 | n = 5; blood glucose value at 0 hr: 140-170 mg/ml; Significantly different from the control, **p < 0.01

The above results reveal that the polysaccharides of aloes have a high hypoglycemic effect.

The results of clinical tests in which the foregoing polysaccharides were administered to patients suffering from diabetes are described below.

CASE 1

Patient: D.T. 63-year-old man
Name of Disease: Diabetes
Treatment History: When he consulted a doctor, he had typical symptoms of diabetes, that is, unhealthy complexion, thirst feeling, thin body (39.2 Kg weight and 172 cm height), dizziness and oversensitiveness of feet and hands to the cold.

To this patient, when at hungry condition, the polysaccharide obtained from Aloe arborescens Mill. in Example 2 was orally administered continuously at a daily dosage of 300 mg in 3 separate doses over three months.

The result of biochemical test is shown in Table 3.

TABLE 3

| | Blood glucose* (mg/dl) | Urine glucose* (g/dl) | Urine protein* (mg/dl) |
|---|---|---|---|
| Before administration | 232 | 3.3 | 20 |
| One month later | 131 | 1.2 | 15 |
| Two months later | 109 | 0.95 | (—) |
| Three months later** | 82 | 0.05 | (—) |

Note:
*All of the data are those when the patient is at hungry condition.
**At this time, thirst feeling, dizziness and oversensitiveness disappeared and the body weight increased by 48 Kg and further the complexion was remarkably improved to the same extent as that of normal people.

CASE 2

Patient: T.T. 61-year-old man
Name of disease: Diabetes and anemia
Treatment History: When he consulted a doctor, he had thirst feeling together with headache, shoulder stiffness and helplessness feeling.

The polysaccharide obtained from Aloe vera L. in Example 1 was orally administered to this patient at hungry condition in the same manner as in the case 1 over four months.

The result of biochemical test is shown in Table 4.

TABLE 4

| | Blood glucose* (mg/dl) | Urine glucose* (g/dl) | Urine protein* (mg/dl) |
|---|---|---|---|
| Before administration | 167 | 2.0 | (—) |
| Four months later** | 101 | (—) | (—) |

Note:
*All of the data are those when the patient is at hungry condition.
**At this time, thirst feeling, headache, shoulder stiffness and helplessness feeling disappeared.

CASE 3

Patient: N.T. 43-year-old man
Name of Disease: Diabetes and pancreatic lithiasis
Treatment History: When he consulted a doctor, he complained of thirst feeling, decrease of vitality and oversensitiveness of feet and hands to the cold.

The polysaccharide obtained from Aloe vera L. in Example 1 was orally administered to this patient at hungry condition in the same manner as in the case 1 over six months.

The result of biochemical test is shown in Table 5.

TABLE 5

| | Blood glucose* (mg/dl) | Urine glucose* (g/dl) | Urine protein* (mg/dl) |
|---|---|---|---|
| Before administration | 213 | 3.2 | (—) |
| Six months later** | 108 | 0.1 | (—) |

Note:
*All of the data are those when the patient is at hungry condition.
**At this time, thirst feeling, decrease of vitality and oversensitiveness of feet and hands to the cold disappeared.

CASE 4

Patient: H.K. 53-year-old woman
Name of Disease: Diabetes and liver complaint
Treatment History: She complained of thirst, severe oversensitiveness of feet and hands to the cold, shoulder stiffness and dizziness.

The polysaccharide contained from Aloe arborescens Mill. in example 2 was orally administered to the patient in the same manner as in the case 1 over 3 months.

The result of biochemical test is shown in Table 6.

TABLE 6

| | Blood sugar* (mg/dl) | Urine sugar* (g/dl) | Urine protein* (mg/dl) |
|---|---|---|---|
| Before administration | 159 | 1.2 | (—) |
| Three months later** | 99 | (—) | (—) |

Note:
*All of the data are those when the patient is at hungry condition.
**At this time, the above mentioned symptoms disappeared.

CASE 5

Patient: A.T. 45-year-old man
Name of Disease: Diabetes
Treatment History: He complained of thirst, shoulder stiffness and decrease of vitality.

The polysaccharide obtained from Aloe arborescens Mill. in example 2 was orally administered to the patient in the same manner as in the above case 1 over six months.

Table 5 shows the results of biochemical test.

TABLE 7

| | Blood glucose* (mg/dl) | Urine glucose* (g/dl) | Urine protein* (mg/dl) |
|---|---|---|---|
| Before administration | 172 | 2.5 | (—) |
| Six months later** | 104 | (—) | (—) |

Note:
*All of the data are those when the patient is at hungry condition.
**At this time, the above symptoms disappeared.

EXAMPLE 3

10 Kg of fresh leaves of Aloe arborescens var. natalensis (Shizuoka, Japan) were slightly washed by cold water and crushed. The resultant was immersed in a mixture of deionized water and methanol (1:1) (20 l×2) at room temperature for extraction for about one day and then extracted with deionized water (20 l×3) at room temperature for one day.

The above extracts were filtered and combined. The combined filtrate was evaporated to about 1 l at 50°–60° C. in vacuo. The concentrate was filtered with suction to remove the insoluble. The filtrate was placed into a cellulose dialyzing membrane, 36/32 type Visking tube, and dialyzed for three days using about 10 l of water as the outer liquid. (The outer liquid was replaced at least once daily). The resulting inner liquid was evaporated to about 100 ml at 50°–60° C. in vacuo.

The obtained concentrate was chromatographed over a Sepharose 6B column (4.0 cm φ×95 cm, from Pharmacia Fine Chemicals) eluting with 0.1M NaCl solution (flow rate 2 ml/mim) to collect continuously fractions of 20 ml.

To 0.2 ml of each of the fractions was added 0.8 ml of water, 1 ml of 5% phenol aqueous solution and 5 ml of sulfuric acid. The fractions showing after 30 mins a higher absorbance λmax at 490 nm (the polysaccharide-rich fractions) were selected and combined.

The combined fractions were concentrated to about 100 ml at 50°–60° C. in vacuo. The resulting concentrate was dialyzed in the same manner as mentioned above.

The resulting inner liquid was evaporated to about 50 ml at 50°–60° C. in vacuo.

The concentrate was chromatographed over a DEAE Toyopearl 650M column (2.2 cm φ×4.5 cm, Toyo Soda Manufacturing Co., LTD.), first eluting with about 2 l of water to collect continuously fractions of 20 ml (G-1) and successively eluting gradiently with 0–0.5M NaCl aqueous solution to collect continuously fractions of 20 ml (G-2).

Each of the G-1 fractions was tested and selected in the same manner as mentioned above. The selected fractions were combined and concentrated to about 30 ml at 50°–60° C. in vacuo.

The concentrate was chromatographed over a Sephacryl S-200 column (4.0 cm φ×95 cm, Pharmacia Fine Chemicals), with eluting 0.1M Tris-HCl buffer (pH 7.0) containing 0.5M NaCL (flow rate 2 ml/min) to collect continuously fractions of 20 ml.

Each of the above fractions was tested and selected in the same manner as mentioned above. The selected fractions were combined and concentrated to about 100 ml at 50°–60° C. in vacuo.

The concentrate was dialyzed in the same manner as mentioned above.

The obtained inner liquid was evaporated to dryness at 50°–60° C. in vacuo to obtain 300 mg of Arboran A as white powder.

On the other hand, each of the fractions (G-2) were tested and selected in the same manner as mentioned above. The selected fractions were combined and concentrated to about 100 ml at 50°–60° C. in vacuo. The concentrate was dialyzed by the same process as mentioned above. The resulting inner liquid was evaporated to about 30 ml at 50°–60° C. in vacuo.

The concentrate was subjected to Chromatogtaphy over a Sephacryl S-200 column eluting with 0.1M Tris-HCl buffer (pH 7.0) containing 0.5M NaCl to collect continuously fractions of 20 ml.

Each of the fractions was tested and selected in the same manner as mentioned above. The selected fractions were combined and concentrated to about 100 ml at 50°–60° C. in vacuo.

The concentrate was dialyzed in the same manner as mentioned above.

The obtained inner liquid was evaporated to dryness at 50°–60° C. in vacuo to obtain 90 mg of Arboran B as white powder.

Arborans A and B have the following properties and also the strong hypoglycemic activity to be stated later.

I Arboran A (a) Solubility: Being soluble in water and insoluble in benzene, ether, chloroform, alcohols and acetone.

(b) Color reaction: Developing a pale yellowish red color on contact with a mixture of 2% aqueous solution of phenol and concentrated sulfuric acid, and being positive for silver mirror reaction and Fehling's solution.

(c) Specific rotation: $[\alpha]_D - 37.7°$ (c 0.13, water).

(d) Elemental analysis: Found: C, 41.11; H, 5.87; N, 0.43%.

(e) Infrared absorption spectrum (KBr method): $\nu$max cm$^{-1}$: 3370, 1726, 1231, 1049, 1027.

(f) NMR spectrum: $^1$H-NMR $\delta$: 2.04, 2.12, 3.72, 4.96, 5.10, 5.43; $^{13}$C-NMR $\delta$: 20.2, 20.4, 60.5, 70.0, 76.6, 172.8, 173.4.

(g) Molecular weight: (standard material: dextran, Sephacryl S-200 gel filtration): $1.2 \times 10^4$.

(h) Glass-fiber paper electrophoresis: (borate buffer, pH 9.3). Moving distance: 17.1 cm (glucose, 10.9 cm).

(i) Polyacrylamide-gel electrophoresis: (10% polyacrylamide gel; borate buffer, pH 9.3). Moving distance: 1.7 cm (bromophenol blue, 8.0 cm)

(j) Neutral sugar content: 44.5% (Phenol —$H_2SO_4$ method); 35.2% (Anthrone —$H_2SO_4$ method); 50.5% (Cromotropic acid —$H_2SO_4$ method).

(k) Uronic acid content: 5.0% (Carbazol —$H_2SO_4$ method).

(l) Peptide content: 2.5% (Lowry method).

(m) O-acetyl content: 16.7%.

(n) Neutral sugar components: Rhamnose-fucose-arabinose-Xylose-mannose-galactose-glucose (0.3:0.2:0.1:0.1:0.2:1.0:0.3).

II Arboran B (a) Solubility: Being soluble in water and insoluble in benzene, ether, chloroform, alcohols and acetone.

(b) Color reaction: Developing a pale yellowish red color on contact with a mixture of 2% aqueous solution of phenol and concentrated sulfuric acid, and being positive for silver mirror reaction and Fehling's solution.

(c) Specific rotation: $[\alpha]_D + 162°$ (C 0.12, water).

(d) Elemental analysis: Found: C, 42.35; H, 5.73; N, 0.26%.

(e) Infrared absorption spectrum (KBr method): $\nu$max cm$^{-1}$: 3350, 1052.

(f) NMR spectrum: $^1$H-NMR $\delta$: 1.21, 3.71, 5.03, 5.20, $^{13}$C-NMR $\delta$: 61.4, 68.7, 70.0, 76.6, 81.0, 81.4, 84.1, 107.5.

(g) Molecular weight: (standard material: dextran, Sephacryl S-200 gel filtration): $5.2 \times 10^4$.

(h) Glass-fiber paper electrophoresis: (borate buffer, pH 9.3). Moving distance: 15.6 cm (glucose 10.9 cm).

(i) Polyacrylamide-gel electrophoresis: (10% polyacrylamide-gel; borate buffer, pH 9.3). Moving distance: 2.7 cm (bromophenol blue, 8.0 cm).

(j) Neutral sugar content: 76.4% (Phenol —$H_2SO_4$ method); 82.0% (Anthrone —$H_2SO_4$ method); 80.0% (Chromotropic acid —$H_2SO_4$ method).

(k) Uronic acid content: 11.5% (Carbazol —$H_2SO_4$ method).

(l) Peptide content: 10.4% (Lowry method).

(m) O-Acetyl content: 5.3%.

(n) Neutral sugar components: Mannose-glucose (0.3:1.0).

Note:

(1) Arborans A and B were dialyzed and chromatographed over Sephadex G-15 with water before analysis.

(2) Glass fiber paper electorphoresis: This was carried out with glass fiber paper (Whatman, GF/C, 15×40 cm) and alkaline borate buffer (pH 9.3) at 450 V for 2 hrs. Visualization was made with the p-anisidine —$H_2SO_4$ reagent.

(3) Polyacrylamide gel electrophoresis: This was performed on 10% polyacrylamide gel columns (0.5 ID×10 cm) with borate buffer of pH 9.3 at 2 m A/tube for 2 hrs. Visualization was done by the thymol —$H_2SO_4$ method and the amidoblack method.

(4) O-acetyl contents: Each of Arborans is hydrolyzed in 1N—HCl at 100° C. for 2 hours and liberated acetic acid is analyzed by a gas chromatography using 3% Thermon 3000 and then the O-acetyl content was calculated.

(5) Neutral sugar components: Each of Arborans is hydrolyzed in 2N—$H_2SO_4$ at 100° C. for 6 hours. The hydrolysate is treated with a conventional manner to obtain alditol acetate. This alditol acetate is analyzed by a gas chromatography using 3% ECNSS-M column to determine the neutral sugar components.

The effect of Arborans A and B on blood glucose value in normal mice and Alloxan-induced Hyperglycemic mice which was determined in the same manner as mentioned above is given in Tables 8 and 9, respectively.

TABLE 8

Effect of Arborans A and B on Blood Glucose Value in Normal Mice

| Drug | Dose (mg/kg) | Relative blood glucose value | | |
|---|---|---|---|---|
| | | 0 | 7 | 24 (hr) |
| Control | — | 100 | 90 ± 4 | 100 ± 5 |
| Arboran A | 10 | 100 | 91 ± 4 | 89 ± 2 |
| | 30 | 100 | 76 ± 6 | 83 ± 1** |
| | 100 | 100 | 69 ± 5** | 78 ± 2** |
| Control | — | 100 | 90 ± 4 | 100 ± 5 |
| Arboran B | 10 | 100 | 91 ± 2 | 79 ± 5** |
| | 30 | 100 | 88 ± 6 | 85 ± 4* |
| | 100 | 100 | 61 ± 2** | 85 ± 4* | n = 5; Blood glucose value at 0 hr: 140–170 mg/ml; Significantly different from the control, *p < 0.05 or **p < 0.01

TABLE 9

Effect of Arborans A and B on Blood Glucose value in Alloxan-included Hyperglycemic Mice

| Drug | Dose (mg/kg) | Relative blood glucose value | | |
|---|---|---|---|---|
| | | 0 | 7 | 24 (hr) |
| Control | — | 100 | 84 ± 5 | 81 ± 4 |
| Arboran A | 10 | 100 | 61 ± 10 | 66 ± 10 |
| | 30 | 100 | 69 ± 7 | 87 ± 5 |
| | 100 | 100 | 51 ± 12* | 87 ± 12 |
| Control | — | 100 | 93 ± 4 | 84 ± 5 |
| Arboran B | 10 | 100 | 98 ± 7 | 94 ± 5 |
| | 30 | 100 | 93 ± 11 | 91 ± 3 |
| | 100 | 100 | 72 ± 14 | 42 ± 11** | n = 5; Blood glucose value at 0 hr: 250–450 mg/ml; Significantly different from the control, *p < 0.05 or **p < 0.01

What is claimed is:

1. A hypoglycemic composition comprising a pharmaceutically acceptable carrier and an active component selected from the group consisting of polysaccharides Arboran A, Arboran B and mixtures thereof, the polysaccharides having hypoglycemic activity and the following properties:

Arboran A (a) solubility: soluble in water and insoluble in benzene, ether, chloroform, alcohols and acetone;

(b) color reaction: developing a pale yellowish red color on contact with a mixture of 2% aqueous solution of phenol and concentrated sulfuric acid, and being positive for silver mirror reaction and Fehling's solution;

(c) specific rotation: $[\alpha]_D - 37.7°$ C 0.13, water);

(d) elemental analysis: C, 41.11; H, 5.87; N, 0.43%;

(e) infrared absorption spectrum (KBr method) $\nu$max cm$^{-1}$: 3370, 1726, 1231, 1049, 1027;

(f) NMR spectrum: $^1$H-NMR $\delta$: 2.04, 2.12, 3.72, 4.96, 5.10, 5.43; $^{13}$C-NMR $\delta$: 20.2, 20.4, 60.5, 70.0, 76.6, 172.8, 173.4;

(g) molecular weight (standard material: dextran, Sephacryl S-200 gel filtration): $1.2 \times 10^4$;
(h) glass-fiber paper electrophoresis (borate buffer, pH 9.3); moving distance: 17.1 cm (glucose, 10.9 cm);
(i) polyacrylamide-gel electrophoresis (10% polyacrylamide gel; borate buffer, pH 9.3); moving distance: 1.7 cm (bromophenol blue, 8.0 cm);
(j) neutral sugar content:
  44.5% (Phenol —$H_2SO_4$ method)
  35.2% (Anthrone —$H_2SO_4$ method)
  50.5% (Cromotropic acid —$H_2SO_4$ method);
(k) uronic acid content (Carbazol —$H_2SO_4$ method): 5.0%;
(l) peptide content (Lowry method): 2.5%;
(m) O-acetyl content: 16.7%;
(n) neutral sugar components: rhamnose-fructose-arabinose-xylose-mannose-galactose-glucose (0.3:0.2:0.1:0.1:0.2:1.0:0.3); and Arboran B
(a) solubility: soluble in water and insoluble in benzene, ether, chloroform, alcohols and acetone;
(b) color reaction: developing a pale yellowish red color on contact with a mixture of 2% aqueous solution of phenol and concentrated sulfuric acid, and being positive for silver reaction and Fehling's solution;
(c) specific rotation: $[\alpha]_D + 162°$ (C 0.12, water);
(d) elemental analysis: C, 42.35; H, 5.73; N, 0.26%;
(e) infrared absorption spectrum (KBr method) $\nu$max cm$^{-1}$: 3350, 1052;
(f) NMR spectrum: $^1$H-NMR $\delta$: 1.21, 3.71, 5.03, 5.20; $^{13}$C-NMR $\delta$: 61.4, 68.7, 70.0, 76.6, 81.0, 81.4, 84.1, 107.5;
(g) molecular weight: (standard material: dextran, Sephacryl S-200 gel filtration): $5.2 \times 10^4$;
(h) glass-fiber paper electrophoresis (borate buffer, pH 9.3); moving distance: 15.6 cm (glucose 10.9 cm);
(i) polyacrylamide-gel electrophoresis (10% polyacrylamide-gel; borate buffer, pH 9.3); moving distance: 2.7 cm (bromophenol blue, 8.0 cm);
(j) neutral sugar content:
  76.4% (Phenol —$H_2SO_4$ method)
  82.0% (Anthrone —$H_2SO_4$ method)
  80.0% (Chromotropic acid —$H_2SO_4$ method);
(k) uronic acid content (Carbazol —$H_2SO_4$ method): 11.5%;
(l) peptide content (Lowry method): 10.4%;
(m) O-acetyl content: 5.3%;
(n) neutral sugar components: Mannose-glucose (0.3; 1.0).

2. A method of treating diabetes which comprises administering to a patient afflicted with diabetes a theraputically effective amount of the composition according to claim 1.

* * * * *